United States Patent [19]

Shono et al.

[11] Patent Number: 5,430,174

[45] Date of Patent: Jul. 4, 1995

[54] METHOD FOR RECOVERING DIMETHYL NAPHTHALENE-2,6-DICARBOXYLATE

[75] Inventors: Hisasi Shono; Kazuhiro Sato, both of Matsuyama; Koji Sumitani, Koganei; Yukio Kuninobu, Matsuyama, all of Japan

[73] Assignee: Teijin Limited, Osaka, Japan

[21] Appl. No.: 258,819

[22] Filed: Jun. 13, 1994

[30] Foreign Application Priority Data

Jun. 16, 1993 [JP] Japan ................... 5-144945

[51] Int. Cl.$^6$ ............................................. C07C 67/48
[52] U.S. Cl. ..................................................... 560/78
[58] Field of Search ........................................ 500/78

[56] References Cited

U.S. PATENT DOCUMENTS 4,876,378 10/1989 Van Sickle ................ 560/78

FOREIGN PATENT DOCUMENTS 50-11381 4/1975 Japan .

WO8911471 11/1989 WIPO .

OTHER PUBLICATIONS

Chemical Abstracts 55:5483e, RN=103272-53-3, 1961.

*Primary Examiner*—José G. Dees
*Assistant Examiner*—Samuel Barts
*Attorney, Agent, or Firm*—Sherman and Shalloway

[57] ABSTRACT

A method for recovering dimethyl naphthalene-2,6-dicarboxylate (DMN) from a mixture of dimethyl naphthalene-2,6-dicarboxylate (DMN) and dimethyl terephthalate (DMT), which comprises recrystallizing said mixture in a mixed medium of ethylene glycol and methanol, said mixed medium containing 10 to 60% by weight of ethylene glycol, and separating precipitated dimethyl naphthalene-2,6-dicarboxylate (DMN). According to this invention, DMN can be recovered with high yield from a mixture of DMN and DMT which is obtained from depolymerization of a mixed polymer of polyethylene-2,6-naphthalenedicarboxylate and polyethylene terephthalate.

6 Claims, No Drawings

METHOD FOR RECOVERING DIMETHYL NAPHTHALENE-2,6-DICARBOXYLATE

FIELD OF THE INVENTION

This invention relates to a method for recovering dimethyl naphthalene-2,6-dicarboxylate (hereinafter abbreviated at times as "DMN") from a mixture of dimethyl naphthalene-2,6-dicarboxylate (DMN) and dimethyl terephthalate (hereinafter abbreviated at times as "DMT"). More specifically, this invention relates to a method for recovering DMN from a mixture of DMN and DMT which is obtained from depolymerization of a mixed polymer containing polyethylene-2,6-naphthalenedicarboxylate and polyethylene terephthalate.

PRIOR ART

Among polyalkylene terephthalate-type polyesters, polyethylene terephthalate has many excellent characteristics, and is, therefore, used in a large amount in a variety of fields such as fibers, films and other molded articles. Further, polyethylene-2,6-naphthalenedicarboxylate is superior to polyethylene terephthalate in heat resistance and mechanical properties, and is attracting attention as a high-performance material for fibers, films and other molded articles. During the polymerization step of these polyethylene terephthalate and polyethylene-2,6-naphthalenedicarboxylate or the step of forming them into yarns, films or other molded articles, defective products, scraps, etc. are formed. In the step of recovering the defective products, the scraps, etc., said polyethylene-2,6-naphthalenedicarboxylate and polyethylene terephthalate are sometimes mixed with each other.

Further, after the molded articles of polyethylene terephthalate and polyethylene- 2,6-naphthalenedicarboxylate are put on the market and actually used up, they are recovered as waste articles. At that time, it is generally difficult to separate polyethylene terephthalate and polyethylene-2,6-naphthalenedicarboxylate as molded articles, and they are recovered in the form of a mixture.

From the standpoint of not only effective reuse of resources but also environmental pollution, it is significant to recover, from a mixed polymer of the aforesaid polyethylene terephthalate and polyethylene-2,6-naphthalenedicarboxylate, their raw materials, above all, the most expensive naphthalene-2,6-dicarboxylic acid component.

A variety of methods for recovering a dicarboxylic acid component by depolymerizing a polyester have been so far known. A method for recovering a naphthalenedicarboxylic acid component in particular by depolymerization of polyethylene naphthalate has been also known. For Example, Japanese Patent Publication No. 11,381/1975 describes a method in which a bisglycol ester of naphthalenedicarboxylic acid is obtained by depolymerizing polyethylene naphthalate with ethylene glycol, and discloses the use of, as a catalyst for depolymerization, at least one compound selected from the group consisting of an alkali metal, an alkaline earth metal, and a hydroxide, an oxide and a weak acid salt of the alkali metal and the alkaline earth metal; an oxide and a weak acid salt of zinc, cadmium, cobalt and lead; and a weak acid salt of manganese.

Japanese Publication of the Translation of International Patent Application No. 3-504,379 (WO 89/11471) discloses a method in which a polyalkylene-2,6-naphthalenedicarboxylate is depolymerized with alcohol or diol in the presence of a catalyst for ester interchange to obtain a dialkyl- 2,6-naphthalenedicarboxylate, and the dialkyl-2,6-naphthalenedicarboxylate is cooled, precipitated and recovered. In said document, it is described that zinc acetate, a tin salt or titanium tetraisopropoxide is effectively used as a catalyst for ester interchange. It is further described that alcohol or diol is used as a depolymerizing agent, and there is a description of alcohol being preferable, but no description on a specific example of using diol. Still further, said document discloses a method to recover a dialkyl-2,6-naphthalenedicarboxylate from not only the polyalkylene-2,6-naphthalenedicarboxylate alone, but also a mixture of it with other polyester, especially polyethylene terephthalate. It is demonstrated solely in Example 4 of said document that the mixture of polyethylene-2,6-naphthalenedicarboxylate and polyethylene terephthalate described in said document is depolymerized with methanol. In said Example 4, the mixture of the aforesaid two polyesters in equal amounts is depolymerized with methanol, the depolymerized mixture is filtered to recover a mixture of 52.4% by weight of DMN and 47.6% by weight of DMT as a solid product, and DMT and DMN are then separated from the solid product by distillation.

Said document discloses, as described above, a method in which DMN and DMT are recovered from the mixed polymer of polyethylene-2,6-naphthalenedicarboxylate and polyethylene terephthalate. This method, when industrially practiced, poses some problems. That is, since the mixed polymer is directly depolymerized with methanol in this method, the reaction must be carried out at a high temperature, and yields of dimethyl terephthalate (DMT) and dimethyl naphthalene-2,6-dicarboxylate (DMN) are low. Further, a high methanol vapor pressure leads to a high reaction pressure which inadvantageously necessitates the use of a pressure-resistant reactor. Still further, when DMT and DMN are fractionally distilled to separate them, the reaction mixture is once cooled, and the precipitated mixture is reheated and distilled at a high temperature of 265° C. For this reason, there is a problem that an energy cost increases. In addition, in performing the fractional crystallization of DMT and DMN, an aromatic compound is used as a solvent. Since a component unrelated to the reaction is thus added, this complicates a step of separating and recovering the solvent, resulting in an increase in cost.

Thus, it is a first object of this invention to provide a method in which expensive DMN is separated and recovered, in high quality and in high recovery rate, from a mixture of DMN and DMT which is obtained by depolymerization of a mixed polymer of polyethylene-2,6-naphthalenedicarboxylate and polyethylene terephthalate.

A second object of this invention is to provide a method comprising a series of steps by which DMN can be recovered in good yield by depolymerization of the mixed polymer at a low energy cost.

A third object of this invention is to provide a simple method for recovering DMN from the mixed polymer without the need of using a specific solvent or complicated means.

Another object of this invention is to provide an industrially advantageous method in which not only DMN but also DMT can be recovered from the mixed polymer.

Still another object of this invention is to provide a method in which a mixed polymer formed during a step of producing polyethylene-2,6-naphthalenedicarboxylate and polyethylene terephthalate or a mixed polymer from spent molded articles formed from polyethylene-2,6-naphthalenedicarboxylate and polyethylene terephthalate can be reused as raw materials thereof without discarding them.

The present inventors conducted a variety of experiments to achieve the foregoing objects of this invention. That is, they made investigations on separation of a naphthalene-2,6-dicarboxylic acid component and a terephthalic acid component from a depolymerized product which is a mixed polymer of polyethylene-2,6-naphthalenedicarboxylate and polyethylene terephthalate. For example, in order to separate bis(hydroxyethyl)-2,6-naphthalenedicarboxylate (BHEN) and bis(hydroxyethyl) terephthalate (BHET) from the depolymerized product obtained by depolymerization of the mixed polymer with ethylene glycol, the depolymerized product was crystallized with water, methanol or glycol. However, none of the solvents could isolate BHEN and BHET in good yields from the depolymerized product.

On the other hand, after excess ethylene glycol was removed from the depolymerized product formed by depolymerization of the mixed polymer with ethylene glycol, the resulting mixture of BHEN and BHET was subjected to an ester interchange reaction with methanol to form a reaction mixture containing DMN and DMT, followed by cooling said reaction mixture. Thus, DMN and DMT could be precipitated as a solid mixture, but could not be obtained with good purities.

In the other experiment, even though the mixture of DMN and DMT was recrystallized in an ethylene glycol solvent, DMN and DMT could not efficiently be separated from each other.

The present inventors further made investigations and as a result, have found that when the mixture of DMN and DMT is recrystallized in a mixed medium containing ethylene glycol and methanol in specific proportions, DMN can be precipitated in good selectivity and separated in high recovery rate. This invention has been achieved on the basis of such findings.

Means for Solving the Problems

In accordance with this invention, the aforesaid objects of this invention can be achieved by a method for recovering dimethyl naphthalene-2,6-dicarboxylate (DMN) from a mixture of dimethyl naphthalene-2,6-dicarboxylate (DMN) and dimethyl terephthalate (DMT), which comprises recrystallizing said mixture in a mixed medium of ethylene glycol and methanol, said mixed medium containing 10 to 60% by weight of ethylene glycol, and separating precipitated dimethyl naphthalene-2,6-dicarboxylate (DMN).

The method of this invention will be explained in more detail below.

In this invention, the mixture of DMN and DMT from which DMN is to be recovered may be one which can be obtained by any method. In general, however, said mixture can be obtained by a depolymerization reaction of a mixed polymer of polyethylene-2,6-naphthalenedicarboxylate and polyethylene terephthalate. The mixture of DMN and DMT resulting from the depolymerization reaction of the mixed polymer is obtained principally by the following two procedures.

Procedure A

A mixed polymer is first depolymerized with ethylene glycol to obtain a reaction mixture containing, as main decomposed materials, bis(hydroxyethyl)-2,6-naphthalenedicarboxylate (BHEN) and bis(hydroxyethyl) terephthalate (BHET), and the reaction mixture is then subjected to ester interchange with methanol to give a mixture containing DMN and DMT.

Procedure B

A mixed polymer is directly decomposed with methanol to give a mixture containing DMN and DMT as main decomposed materials.

Said procedures A and B are typical ones in which the mixture containing DMN and DMT is obtained by the depolymerization of the mixed polymer. However, since the mixed polymer is directly reacted with methanol in the procedure B, the decomposition temperature is high and decomposition of methanol is unavoidable. Further, the yields of DMN and DMT in the procedure B are not said to be sufficient. Still further, in the procedure B, a high methanol vapor pressure leads to a high reaction pressure which inadvantageously necessitates the use of a pressure-resistant reactor. Accordingly, the procedure A is industrially superior to the procedure B for recovering DMN and DMT from the mixed polymer. Especially, when the procedure A is conducted under the conditions and the selection of a catalyst later described. It is all the more advantageous industrially because the reaction conditions are mild and the recovery rate and purity of the intended methyl ester are high.

The mixture from which DMN is to be separated as a solid by crystallization in accordance with the method of this invention may be a mixture containing DMN and DMT. In this case, the suitable proportion (weight ratio) of DMN and DMT is 20:80 to 95:5, preferably 30:70 to 90:10. Therefore, when the mixture containing DMN and DMT is obtained by depolymerization, a suitable mixed polymer is required to contain polyethylene-2,6-naphthalenedicarboxylate and polyethylene terephthalate such that DMN and DMT become contained at the above ratio.

A method in which the mixed polymer is depolymerized by the procedure A and DMN and DMT are recovered will be described hereinafter. The following description is concerned with the preferable reaction conditions and catalyst, and it is, therefore, possible to modify the conditions and use other catalysts as required.

Polyethylene-2,6-naphthalenedicarboxylate in the mixed polymer may usually be one which can be used in fibers, films and other molded articles. Said polyethylene-2,6-naphthalenedicarboxylate comprises a 2,6-naphthalenedicarboxylic acid component and an ethylene glycol component, and part of said components may be replaced with one or more compounds selected from difunctional acids such as 2,7-naphthalenedicarboxylic acid, 1,5-naphthalenedicarboxylic acid, terephthalic acid, isophthalic acid, p-hydroxybenzoic acid and diphenyldicarboxylic acid, and aliphatic, alicyclic and aromatic dihydroxy compounds such as trimethylene glycol, 1,4-butanediol and bisphenol A. Further, the terminal(s) of said polymer may be bound to a monofunctional compound such as benzyloxybenzoic acid.

The polymer may contain a stabilizer such as phosphoric acid, phosphorous acid or their esters, or other additives.

Polyethylene terephthalate which is the other polymer component in the mixed polymer may usually be one which can be used in fibers, films and other molded articles. Said polyethylene terephthalate comprises a terephthalic acid component and an ethylene glycol component, and part of said components may be replaced with one or more compounds selected from difunctional acids such as isophthalic acid, diphenyldiarboxylic acid, p-hydroxybenzoic acid. 2,6-naphthalenedicarboxylic acid and 2,7-naphthalenedicarboxylic acid and the above dihydroxy compound.

When the mixed polymer is first depolymerized with ethylene glycol according to the procedure A, preferred examples of the catalyst for depolymerization are (a) an alkali metal, alkaline earth metal, and a hydroxide, an oxide and a weak acid salt of the alkali metal and the alkaline earth metal, (b) an oxide and a weak acid salt of zinc and cobalt, and (c) a weak acid salt of manganese. Examples of the weak acid salts are a carbonate, a bicarbonate, an acetate and a propionate. Specific examples of the catalyst include sodium carbonate, sodium bicarbonate, sodium acetate, sodium propionate, potassium carbonate, potassium bicarbonate, potassium acetate, potassium propionate, calcium carbonate, calcium bicarbonate, calcium acetate, calcium propionate, magnesium acetate, magnesium propionate, zinc acetate, zinc propionate, sodium hydroxide, sodium oxide, manganese acetate and cobalt acetate.

They may be used either singly or in admixture of two or more. Of the above catalysts, sodium carbonate and sodium bicarbonate are especially preferable. The amount of the catalyst is 0.0005 to 20% by weight, preferably 0.001 to 10% by weight, based on the total weight of polyethylene-2,6-naphthalenedicarboxylate and polyethylene terephthalate.

The amount of ethylene glycol used in the depolymerization reaction may be equivalent to, or larger than, the total amount of the recurring units of polyethylene-2,6-naphthalenedicarboxylate and polyethylene terephthalate. It is usually at least 0.32 time (by weight), preferably 0.7 to 7.0 times (by weight), as large as the total weight of polyethylene-2,6-naphthalenedicarboxylate and polyethylene terephthalate. A small amount of an oligomer of polyethylene terephthalate may be contained in ethylene glycol.

When the depolymerization temperature is too high in the depolymerization reaction of the mixed polymer with ethylene glycol, the side reaction tends to notably occur. For example, at the polymerization temperature of 250° C., the depolymerization reaction advances with the polymerization catalyst present in the polymer without newly adding the catalyst, to give a mixture of a monomer, a dimer and a trimer (monomer is an oligomer containing one naphthalene ring). However, due to the side reaction, an excess of the catalyst is required in the subsequent ester interchange reaction, or the yields of DMN and DMT become low. On the other hand, when the depolymerization reaction temperature is too low, the reaction requires much time. The depolymerization reaction temperature is, therefore, usually 180° to 235° C., preferably 190° to 230° C. Said reaction proceeds either under atmospheric pressure or under increased pressure, and can be conducted either batchwise or continuously.

Even if the reaction product resulting from the depolymerization reaction of the mixed polymer with ethylene glycol contains excess ethylene glycol, it is unnecessary to remove said excess ethylene glycol to give a composition having high contents of BHEN and BHET. Rather, without removing ethylene glycol, said reaction product can be subjected, as such, to the subsequent ester interchange reaction with methanol.

The amount of methanol used in the ester interchange reaction may be at least 2 molar times as large as the total molar amount of recurring units of polyethylene-2,6-naphthalenecarboxylate and polyethylene terephthalate, and is usually preferably 2 to 10 times (by weight) as large as the total weight of polyethylene-2,6-naphthalenedicarboxylate and polyethylene terephthalate.

Preferred examples of the catalyst used in the ester interchange reaction include a carbonate and a bicarbonate of an alkali metal and an alkaline earth metal. Specific examples of such a catalyst include sodium carbonate, sodium bicarbonate, potassium carbonate, potassium bicarbonate, calcium carbonate and calcium bicarbonate. They may be used either singly or in admixture of two or more. Of the above catalysts, sodium carbonate and sodium bicarbonate are preferable. The amount of the catalyst is usually 0.01 to 20% by weight, preferably 0.4 to 4% by weight, based on the total weight of polyethylene-2,6-naphthalenedicarboxylate and polyethylene terephthalate.

When the reaction temperature in the ester interchange reaction is too high, the side reaction notably occurs, and the yields of DMN and DMT decrease. This is presumably because the side reaction such as hydrolysis or the like proceeds all the more at the high reaction temperature. By conducting the reaction at a low reaction temperature, DMN and DMT can easily be obtained in good yields. Accordingly, the reaction temperature is usually 30° to 100° C., preferably 50° to 80° C. This reaction proceeds either under atmospheric pressure or under increased pressure, and can be conducted either batchwise or continuously.

When the mixture containing DMN and DMT which is obtained by the depolymerization in the procedure A is crystallized, DMN is precipitated as a solid crystal. On that occasion, it is necessary that the contents of ethylene glycol and methanol in the depolymerized mixture are adjusted to predetermined ranges. That is, in order to precipitate DMN as a solid in good yield with good purity from the depolymerized mixture of DMN and DMT, it is important that the mixed medium of ethylene glycol and methanol contains 10 to 60% by weight of ethylene glycol and 90 to 40% by weight of methanol. A preferable mixed medium contains 15 to 50% by weight of ethylene glycol and 85 to 50% by weight of methanol.

The depolymerized mixture obtained by the procedure A contains ethylene glycol formed by the decomposition of the mixed polymer and excess methanol used in the ester interchange reaction. It is required that the contents of ethylene glycol and methanol in the depolymerized mixture are examined and adjusted to the above ranges before the crystallization. When the contents of ethylene glycol and methanol meet the above ranges, it is, of course, not necessary to adjust said contents, and the depolymerized mixture can be directly subjected to the crystallization.

In the crystallization, the amount of the mixed medium varies mainly depending on the amount of DMN contained in the depolymerized mixture. It is generally 2 to 12 times (by weight), preferably 3 to 10 times (by weight), as large as the total weight of DMN and DMT.

In the crystallization, a temperature at which to heat the depolymerized mixture of DMN and DMT in the mixed medium is 64° to 150° C., preferably 70° to 130° C. When the heated solution is cooled to a temperature of 50° C. or lower, preferably 30° to 45° C., DMN is precipitated as a solid crystal.

When the heated solution is cooled to the above cooling temperature and the precipitated solid is subjected to solid-liquid separation, a major part of DMN is separated as a separated cake, while a major part of DMT is dissolved and present in the separated liquid. When the amount of DMT in the heated solution before crystallization is relatively larger than the amount of DMN, a part of DMT is sometimes precipitated by crystallization and incorporated in the DMN cake. In that case, the obtained cake is recrystallized in a mixed medium of the same composition as that of the above mixed medium or in a methanol medium, whereby purity of DMN can be improved. The recrystallization can be conducted once or more times. The number of the recrystallization(s) is properly determined depending on the content of DMT in the cake, the contents of impurities, and the desired purity of DMN.

The separated liquid in the crystallization contains a major part of DMT and a part of DMN. Accordingly, in order to recover DMT from the separated liquid, the separated liquid may be distilled to remove low-boiling fractions such as methanol, ethylene glycol, etc., and DMT be then separated by distillation.

EXAMPLES

This invention will be illustrated more specifically by referring to the following Examples and Comparative Examples.

Example 1

A 2-liter stainless steel autoclave equipped with an electromagnetic induction-type stirrer was charged with a mixture of 187.0 g of polyethylene-2,6-naphthalenedicarboxylate (PEN) and 33 g of polyethylene terephthalate (PET), 350 g of ethylene glycol (EG) and 2.2 g of anhydrous sodium carbonate ($Na_2CO_3$) as a catalyst for depolymerization, and the reaction was conducted at 200° C. for 6 hours to obtain a depolymerized mixture. Subsequently, 300 g of the depolymerized mixture was taken, and after addition of 690 g of methanol and 2.32 g of $Na_2CO_3$ thereto, an ester interchange reaction was conducted at 70° C. for 2 hours. Then, the reaction mixture was cooled to 43° C. to crystallize dimethyl naphthalene-2,6-dicarboxylate (DMN), and the mixture was filtered to give 106.8 g of a DMN crude crystal (dimethyl terephthalate (DMT) concentration=0.148 % by weight) and a filtrate (DMT concentration=1.22 % by weight). Thereafter, 75.9 g of the DMN crude crystal was taken, and 340.0 g of methanol was added thereto. After the temperature was raised to 130° C., the mixture was gradually cooled to 40° C. for recrystallization. When the recrystallized mixture was subjected to solid-liquid separation by filtration, there were obtained 69.6 g of a DMN crystal (DMT concentration=0.02 % by weight) and 396.6 g of a filtrate (DMT concentration=0.14 % by weight).

Examples 2 to 9

Forty (40) grams of EG and 0.2 g of $Na_2CO_3$ were added to 20 g of each of eight kinds of mixtures of PEN and PET having different PET concentrations [PET/(PEN+PET)] of 10, 15, 20, 30, 40, 50, 60 and 70% by weight, and a depolymerization reaction was conducted at 200° C. at atmospheric pressure for 6 hours. Then, 120 g of methanol and 0.2 g of $Na_2CO_3$ were added to the resulting depolymerized mixture, and an ester interchange reaction was carried out at 70° C. at atmospheric pressure for 2 hours. Thereafter, the reaction mixture was gradually cooled to 40° C. to crystallize DMN, and the mixture was subjected to solid-liquid separation by filtration to obtain a crude crystal of an ester interchange filtered cake. Subsequently, 120 g of methanol was added to the crude crystal, and the temperature was elevated to 130° C. The mixture was then gradually cooled to 40° C. for recrystallization. The recrystallized mixture was subjected to solid-liquid separation by filtration to obtain a recrystallized, filtered cake. The results are shown in Table 1.

TABLE 1

| Example No. | 2 | 3 | 4 | 5 | 6 | 7 | 8 | 9 |
|---|---|---|---|---|---|---|---|---|
| PET concentration in a raw material [((PET/(PET+PET))]wt. % | 10 | 15 | 20 | 30 | 40 | 50 | 60 | 70 |
| DMT concentration in an ester Interchange filtered cake (wt. %) | 2.44 | 6.73 | 9.02 | 21.4 | 27.8 | 41.5 | 51.9 | 62.6 |
| DMT concentration in a recrystallized filtered cake (wt. %) | 0.02 | 0.05 | 0.06 | 8.80 | 14.7 | 30.0 | 45.7 | 59.5 |
| Recovery rate of DMN (mol. %) | 91.8 | 89.1 | 87.1 | 85.8 | 86.0 | 84.0 | 84.9 | 83.9 |

Examples 10 to 12

To a mixture of 160.0 g of PEN and 40.0 g of PET were added 400 g of EG and 2.0 g of $Na_2CO_3$, and a depolymerization reaction was conducted at 200° C. at atmospheric pressure for 6 hours. Then, 1,200 g of methanol and 2.0 g of $Na_2CO_3$ were added to the depolymerized mixture, and an ester interchange reaction was performed at 70° C. at atmospheric pressure for 2 hours. Thereafter, the reaction mixture was gradually cooled to 40° C. to crystallize DMN, and the mixture was subjected to solid-liquid separation by filtration to obtain 164 g of a crude crystal of an ester interchange filtered cake (DMT concentration=8.5% by weight). Subsequently, 32.8 g of the crude crystal was taken, and methanol was added thereto in varying amounts of 200 g, 160 g and 120 g respectively. After the temperature was elevated to 130° C., each of the mixtures was gradually cooled to 40° C. for recrystallization. The recrystallized mixture was subjected to solid-liquid separation by filtration to obtain a recrystallized, filtered cake. The results are shown in Table 2.

TABLE 2

| Example No. | 10 | 11 | 12 |
|---|---|---|---|
| PET concentration in a raw material (PET/(PET+PEN))wt. % | 20 | 20 | 20 |
| DMT concentration in an ester interchange filtered cake (wt. %) | 8.50 | 8.50 | 8.50 |
| DMT concentration in a recrystallized, filtered cake (wt. %) | 0.08 | 0.10 | 0.13 |
| Recovery rate of DMN (mol. %) | 88.0 | 88.1 | 88.5 |

Examples 13 to 15

A 700-milliliter stainless steel autoclave equipped with an electromagnetic induction-type stirrer was charged with a mixture of 20 g of polyethylene-2,6-naphthalenedicarboxylate (PEN) and 20 g of polyethylene terephthalate (PEN) and 0.04 g of manganese acetate as a catalyst for depolymerization. Methanol was added in varying amounts of 80 g, 160 g and 240 g. Each of the mixtures was allowed to react with stirring at a reaction temperature of 200° C. over a period of 3.0 hours. Final reaction pressures were about 27, about 30 and about 39 kg/cm³G respectively. After the reaction terminated, the reaction mixture was cooled to 40° C. over a period of 1.5 hours. The reaction mixture was taken out, and subjected to solid-liquid separation by filtration using a glass filter (G-3). To the obtained ester interchange filtered cake were added 130 g of methanol and 30 g of ethylene glycol. After the temperature was elevated to 130° C., the mixture was gradually cooled to 40° C. for recrystallization. The recrystallized mixture was subjected to solid-liquid separation by filtration to obtain a recrystallized, filtered cake. The results are shown in Table 3.

TABLE 3

| Example No. | 13 | 14 | 15 |
|---|---|---|---|
| DMT concentration in an ester interchange filtered cake (wt. %) | 44.4 | 42.0 | 39.7 |
| DMT concentration in a recrystallized, filtered cake (wt. %) | 31.5 | 29.5 | 26.5 |
| Recovery rate of DMN (mol. %) | 86.0 | 85.1 | 84.1 |

Comparative Examples 1 to 3

A 700-milliliter stainless steel autoclave equipped with an electromagnetic induction-type stirrer was charged with a mixture of 20 g of polyethylene-2,6-naphthalenedicarboxylate (PEN) and 20 g of polyethylene terephthalate (PET) and 0.04 g of manganese acetate as a catalyst for depolymerization. Methanol was added in varying amounts of 80 g, 160 g and 240 g. Each of the mixtures was allowed to react with stirring at a reaction temperature of 200° C. over a period of 3.0 hours. Final reaction pressures were about 27, about 30 and about 39 kg/cm³G. After the reaction terminated, the mixture was cooled to 28° C. over a period of 1.5 hours. The reaction mixture was taken out and subjected to solid-liquid separation by filtration using a glass filter (G-3). To the resulting ester interchange filtered cake was added 160 g of methanol. After the temperature was elevated to 130° C., the mixture was gradually cooled to 40° C. for recrystallization. The recrystallized mixture was subjected to solid-liquid separation by filtration to obtain a recrystallized, filtered cake. The results are shown in Table 4.

TABLE 4

| Comparative Example No. | 1 | 2 | 3 |
|---|---|---|---|
| DMT concentration in an ester interchange filtered cake (wt. %) | 49.7 | 46.6 | 45.5 |
| DMT concentration in a recrystallized, filtered cake (wt. %) | 36.5 | 34.0 | 32.5 |
| Recovery rate of DMN (mol. %) | 86.5 | 85.0 | 85.1 |

Examples 16 to 23

A 700-milliliter stainless steel autoclave equipped with an electromagnetic induction-type stirrer was charged with 100 g of a mixture of DMN and DMT (the DMT content of 30% by weight) and 400 g of methanol or a mixed solvent of methanol and EG. After the temperature was raised to 130° C., the mixture was gradually cooled. The temperature of terminating the cooling was varied within the range of 20° to 40° C. The recrystallized mixture was subjected to solid-liquid separation by filtration at the same temperature as the temperature of terminating the cooling. There was obtained a recrystallized, filtered cake. The results are shown in Table 5.

TABLE 5

| Example No. | 16 | 17 | 18 | 19 | 20 | 21 | 22 | 23 |
|---|---|---|---|---|---|---|---|---|
| EG content in a recrystallization solvent (%) | 0 | 15 | 20 | 30 | 50 | 30 | 30 | 70 |
| Temperature of terminating the cooling (°C.) | 40 | 40 | 40 | 40 | 40 | 20 | 30 | 40 |
| DMT concentration In a recrystallized filtered cake (wt. %) | 28.0 | 23.0 | 22.6 | 22.8 | 23.8 | 28.6 | 25.7 | 23.9 |
| Recovery rate of DMN (mol. %) | 95.9 | 95.4 | 92.3 | 94.1 | 93.1 | 96.3 | 95.5 | 83.0 |

What we claim is:

1. A method for recovering dimethyl naphthalene-2,6-dicarboxylate (DMN) from a mixture of dimethyl naphthalene-2,6-dicarboxylate (DMN) and dimethyl terephthalate (DMT), which comprises recrystallizing said mixture in a mixed medium of ethylene glycol and methanol, said mixed medium containing 10 to 60% by weight of ethylene glycol, and separating precipitated dimethyl naphthalene-2,6-dicarboxylate (DMN).

2. The method of claim 1 wherein said mixture is a reaction product which is obtained by depolymerizing a mixed polymer of polyethylene-2,6-naphthalenedicarboxylate and polyethylene terephthalate with ethylene glycol and then subjecting the resulting depolymerized mixture to an ester interchange reaction with methanol.

3. The method of claim 1 wherein said mixture is a reaction product which is obtained by depolymerizing a mixed polymer of polyethylene-2,6-naphthalenedicarboxylate and polyethylene terephthalate with methanol.

4. The method of claim 1 wherein the ratio of dimethyl naphthalene-2,6-dicarboxylate:dimethyl terephthalate is within the range of 20:80 to 95:5 by weight.

5. The method of claim 1 wherein the ethylene glycol content in the mixed medium is 15 to 50% by weight.

6. The method of claim 1 wherein said mixture is a reaction product which is obtained by depolymerizing a mixed polymer of polyethylene-2,6-naphthalenedicarboxylate and polyethylene terephthalate with ethylene glycol in the presence of at least one compound, as a catalyst, selected from the group consisting of (a) an alkali metal, alkaline earth metal, and a hydroxide, an oxide and a weak acid salt of the alkali metal and the alkaline earth metal, (b) an oxide and a weak acid salt of zinc and cobalt and (c) a weak acid salt of manganese, and then subjecting the depolymerized product to an ester interchange reaction with methanol in the presence of a catalyst selected from the group consisting of a carbonate and a bicarbonate of an alkali metal and alkaline earth metal.

* * * * *